United States Patent
Atalla et al.

(10) Patent No.: US 12,364,463 B2
(45) Date of Patent: Jul. 22, 2025

(54) MECHANICAL SHEAR WAVE GENERATION FOR ULTRASONIC ELASTOGRAPHY

(71) Applicant: KONINKLIJKE PHILIPS N.V., Eindhoven (NL)

(72) Inventors: Mostafa Abdelaziz Ali Atalla, Rijswijk (NL); Ramon Quido Erkamp, Swampscott, MA (US); Man M Nguyen, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 123 days.

(21) Appl. No.: 17/923,962

(22) PCT Filed: May 7, 2021

(86) PCT No.: PCT/EP2021/062105
§ 371 (c)(1),
(2) Date: Nov. 8, 2022

(87) PCT Pub. No.: WO2021/228698
PCT Pub. Date: Nov. 18, 2021

(65) Prior Publication Data
US 2023/0181162 A1      Jun. 15, 2023

Related U.S. Application Data

(60) Provisional application No. 63/022,597, filed on May 11, 2020.

(51) Int. Cl.
*A61B 8/00*       (2006.01)
*A61B 5/00*       (2006.01)

(52) U.S. Cl.
CPC ............ *A61B 8/485* (2013.01); *A61B 5/0051* (2013.01); *A61B 8/42* (2013.01)

(58) Field of Classification Search
CPC .......... A61B 8/485; A61B 5/0051; A61B 8/42
See application file for complete search history.

(56) References Cited

U.S. PATENT DOCUMENTS

| | | |
|---|---|---|
| 5,606,971 A | 3/1997 | Sarvazyan |
| 5,810,731 A | 9/1998 | Sarvazyan et al. |

(Continued)

FOREIGN PATENT DOCUMENTS

| | | | |
|---|---|---|---|
| WO | WO-2010143555 A1 * | 12/2010 | ............... A61B 8/08 |
| WO | 2013026141 A1 | 2/2013 | |
| WO | 2018191381 A1 | 10/2018 | |

OTHER PUBLICATIONS

International Search Report and Written Opinion for PCT/EP2021/062105; Mailing date: Aug. 13, 2021, 10 pages.

(Continued)

*Primary Examiner* — Chao Sheng

(57) ABSTRACT

An ultrasonic diagnostic imaging system performs elastography using mechanically generated vibrations from a vibration assembly attached to an ultrasound probe. An attachment member attaches the vibration assembly to the probe. A vibration motor is mounted in a motor mount and applies vibration energy to the body in which shear waves are to be measured, at a location adjacent to the probe. The vibration motor mount is coupled to the attachment member by a vibration isolation element such as a spring, rubber band, or elastic compound which isolates the probe from deleterious vibration energy from the vibration motor.

19 Claims, 4 Drawing Sheets

(56) References Cited

U.S. PATENT DOCUMENTS

| | | | | |
|---|---|---|---|---|
| 2009/0306515 | A1* | 12/2009 | Matsumura | A61B 8/4281 600/459 |
| 2014/0033052 | A1 | 1/2014 | Kaufman et al. | |
| 2014/0330122 | A1* | 11/2014 | Baghani | A61B 8/463 600/438 |
| 2021/0196234 | A1* | 7/2021 | Yang | G01S 7/52042 |

OTHER PUBLICATIONS

Yang, H. et al., "Simulation, design, and implementation of external mechanical vibration for ultrasound shear wave elastography", IEEE International Ultrasonics Symposium (IUS), 2017, pp. 1-4.

Van de Donk, F. et al., "Miniaturization of External Mechanical Vibration for Shear Wave Elastography Imaging," 2018 40th Annual International Conference of the IEEE Engineering in Medicine and Biology Society (EMBC), 2018, pp. 3464-3467.

Yang, H., "Ultrasound shear wave elastography imaging with external mechanical vibration", Thesis: S.M., Massachusetts Institute of Technology, Department of Mechanical Engineering, 2017, 108 pages.

Yamakoshi, Y. et al., "Ultrasonic imaging of internal vibration of soft tissue under forced vibration", IEEE Transactions on Ultrasonics, Ferroelectrics, and Frequency Control, 1990, vol. 37, No. 2, pp. 45-53.

Zhao, H. et al., "External Vibration Multi-directional Ultrasound Shearwave Elastography (EVMUSE): Application in Liver Fibrosis Staging", IEEE Trans Med Imaging, 2014, vol. 33, pp. 2140-2148.

Mellema, D.C. et al., "Probe Oscillation Shear Elastography (PROSE): A High Frame-Rate Method for Two-Dimensional Ultrasound Shear Wave Elastography", IEEE Trans Med Imaging, 2016, vol. 35, pp. 2098-2106.

Ormachea, J. et al., "Shear Wave Speed Estimation Using Reverberant Shear Wave Fields: Implementation and Feasibility Studies", Ultrasound Med Biol., 2018, vol. 44, pp. 963-977.

* cited by examiner

MECHANICAL SHEAR WAVE GENERATION FOR ULTRASONIC ELASTOGRAPHY

CROSS-REFERENCE TO PRIOR APPLICATIONS

This application is the U.S. National Phase application under 35 U.S.C. § 371 of International Application No. PCT/EP2021/062105, filed on May 7, 2021, which claims the benefit of U.S. Provisional Patent Application No. 63/022,597, filed on May 11, 2020. These applications are hereby incorporated by reference herein.

This invention relates to medical diagnostic ultrasound systems and, in particular, to ultrasound systems which perform measurements of tissue stiffness or elasticity using shear waves.

One of the long-sought goals of diagnostic ultrasound is precise tissue characterization. Ideally, a clinician would like to scan a diagnostic region of an organ of the body and have the ultrasound system identify the characteristics of the tissue in an image. For instance, a clinician would like the ultrasound system to identify a lesion as malignant or benign. While fully obtaining this objective remains yet to be accomplished, diagnostic ultrasound can nonetheless give the clinician clues as to the makeup of tissue. One technique in this area is elastography, which measures the elasticity or stiffness of tissues in the body. For example, breast tumors or masses with high stiffness might be malignant, whereas softer and more compliant masses are likely to be benign. Since the stiffness of a mass is known to correlate with malignancy or benignity, elastography provides the clinician with another piece of evidence to aid in diagnosis and determination of a treatment regimen.

Elastography as initially contemplated assessed tissue in the body when subjected to compressive pressure. When an ultrasound probe is pressed firmly against the body, underlying soft tissue will compress to a greater degree than underlying hard tissue. But probe pressure can be very operator-dependent, with results being influenced by where and how much pressure is being applied to the body. It would be desirable to be able to assess elasticity by a method which is not so operator-dependent.

An alternate approach to elasticity measurement is to use transmitted ultrasound to produce a shear wave for measurement. When a point on the body is compressed, then released, the underlying tissue is compressed downward, then rebounds back up when the compressive force is released. But since the tissue under the compressive force is continuously joined to surrounding tissue, the uncompressed tissue lateral of the force vector will respond to the up-and-down movement of the compressed tissue. A rippling effect in this lateral direction, referred to as a shear wave, is the response in the surrounding tissue to the downward compressive force. It has been found that the force needed to push the tissue downward can be produced by the radiation pressure from the acoustic radiation force of an ultrasound pulse, and ultrasound reception can be used to sense and measure the tissue motion induced by the shear waves. Shear wave velocity is determined by local tissue mechanical properties. The shear wave will travel at one velocity through soft tissue, and at another, higher velocity through hard tissue. By measuring the velocity of the shear wave at a point in the body, information is obtained as to characteristics of the tissue such as its shear elasticity modulus, Young's modulus, and dynamic shear viscosity. The laterally propagating shear wave travels slowly, usually a few meters per second or less, making the shear wave susceptible to detection, although it attenuates rapidly over a few centimeters or less. See, for example, U.S. Pat. No. 5,606,971 (Sarvazyan) and U.S. Pat. No. 5,810,731 (Sarvazyan et al.) Since the same acoustic "push pulse" can be repeated for each measurement, the shear wave technique lends itself to objective quantification of tissue characteristics with ultrasound. Furthermore, the shear wave velocity is independent of the push pulse intensity, making the measurement less dependent upon the user.

Shear wave elastography has become a common feature on premium ultrasound imaging systems, where the shear wave is generated with a special long acoustic push pulse, and tracked using imaging beams. The push pulse for shear wave generation is transmitted at a high power for an extended duration. The ability to generate such a pulse creates special requirements for imaging probe design and transducer driving electronics. As a consequence, shear wave elastography is generally available on a limited selection of imaging probes on more expensive, high-end ultrasound systems.

Shear waves can also be generated by applying a mechanical vibrator to the body, avoiding the need for special requirements for probe design and driving electronics. This allows the implementation of shear wave elastography on a larger family of ultrasound imaging platforms and probes that currently are not capable of performing elastography. It is an object of the present invention to provide a mechanical vibrator assembly for an ultrasound probe which generates the desired shear waves in a body without coupling significant unwanted vibratory frequencies to the probe itself, which can corrupt the reception of desired measurement echoes from measurement pulses.

In accordance with the principles of the present invention, a diagnostic ultrasound system is described which enables a user to apply shear waves to a body with a mechanical vibrator without coupling significant deleterious vibratory energy into the ultrasound probe used to measure the shear waves. A vibrator assembly comprises a probe attachment element which is adapted to attach the vibrator assembly to an ultrasound probe which operates to measure shear waves. A vibration motor assembly is coupled to the probe attachment element by a vibration isolation element which acts to isolate the probe attachment element and hence the probe from unwanted vibration energy.

Figure 1:
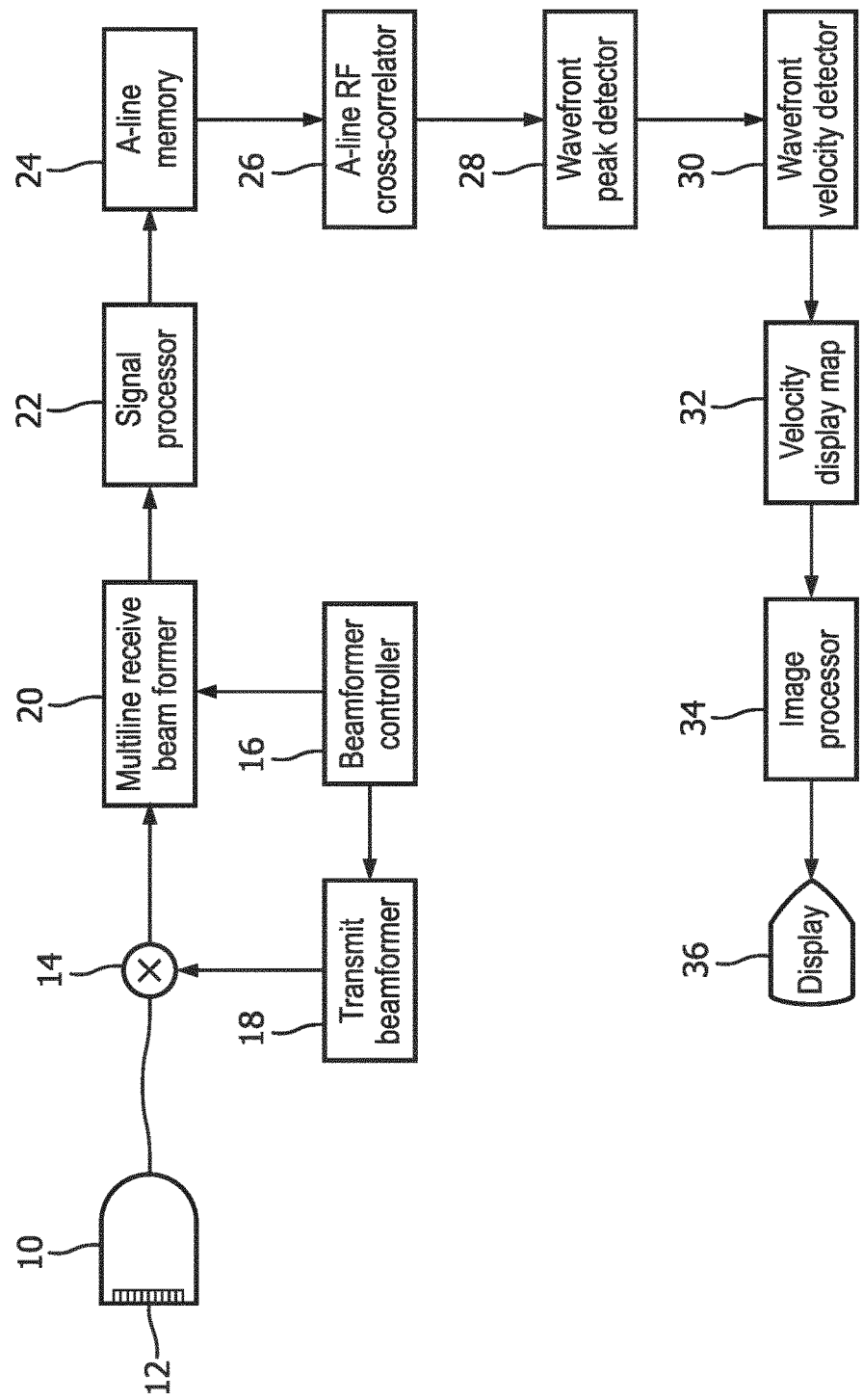
FIG. 1 illustrates in block diagram form an ultrasonic diagnostic system for shear wave analysis constructed in accordance with the principles of the present invention.

Referring first to FIG. 1, an ultrasound system constructed in accordance with the principles of the present invention for the measurement of shear waves is shown in block diagram form. An ultrasound probe 10 has a transducer array 12 of transducer elements for transmitting and receiving ultrasound signals. The array can be a one dimensional or a two-dimensional array of transducer elements. Either type of array can scan a 2D plane and the two-dimensional array can be used to scan a volumetric region in front of the array. The array elements are coupled to a transmit beamformer 18 and a multiline receive beamformer 20 by a transmit/receive (T/R) switch 14. Coordination of transmission and reception by the beamformers is controlled by a beamformer controller 16. The multiline receive beamformer produces multiple, spatially distinct receive lines (A-lines) of echo signals during a single transmit-receive interval. The echo signals are processed by filtering, noise reduction, and the like by a signal processor 22, then stored in an A-line memory 24. Temporally distinct A-line samples relating to the same spatial vector location are associated with each other in an ensemble of echoes relating to a common point in the image field. The r.f. echo signals of successive A-line sampling of the same spatial vector are cross-correlated by an A-line r.f. cross-correlator 26 to produce a sequence of samples of tissue displacement for each sampling point on the vector. Alternatively, the A-lines of a spatial vector can be Doppler processed to detect shear wave motion along the vector, or other phase-sensitive techniques can be employed. A wavefront peak detector 28 is responsive to detection of the shear wave displacement along the A-line vector to detect the peak of the shear wave displacement at each sampling point on the A-line. In a preferred embodiment this is done by curve-fitting, although cross-correlation and other interpolative techniques can also be employed if desired. The time at which the peak of the shear wave displacement occurs is noted in relation to the times of the same event at other A-line locations, all to a common time reference, and this information is coupled to a wavefront velocity detector 30 which differentially calculates the shear wave velocity from the peak displacement times on adjacent A-lines. This velocity information is coupled into a velocity display map 32 which indicates the velocity of the shear wave at spatially different points in a 2D or 3D image field. The velocity display map is coupled to an image processor 34 which processes the velocity map, preferably overlaying the anatomical ultrasound image of the tissue, for display on an image display 36.

It will be appreciated that a standard beamformer which receives only a single scanline in response to an interrogating pulse may also be used in an implementation of the present invention.

Figure 2:
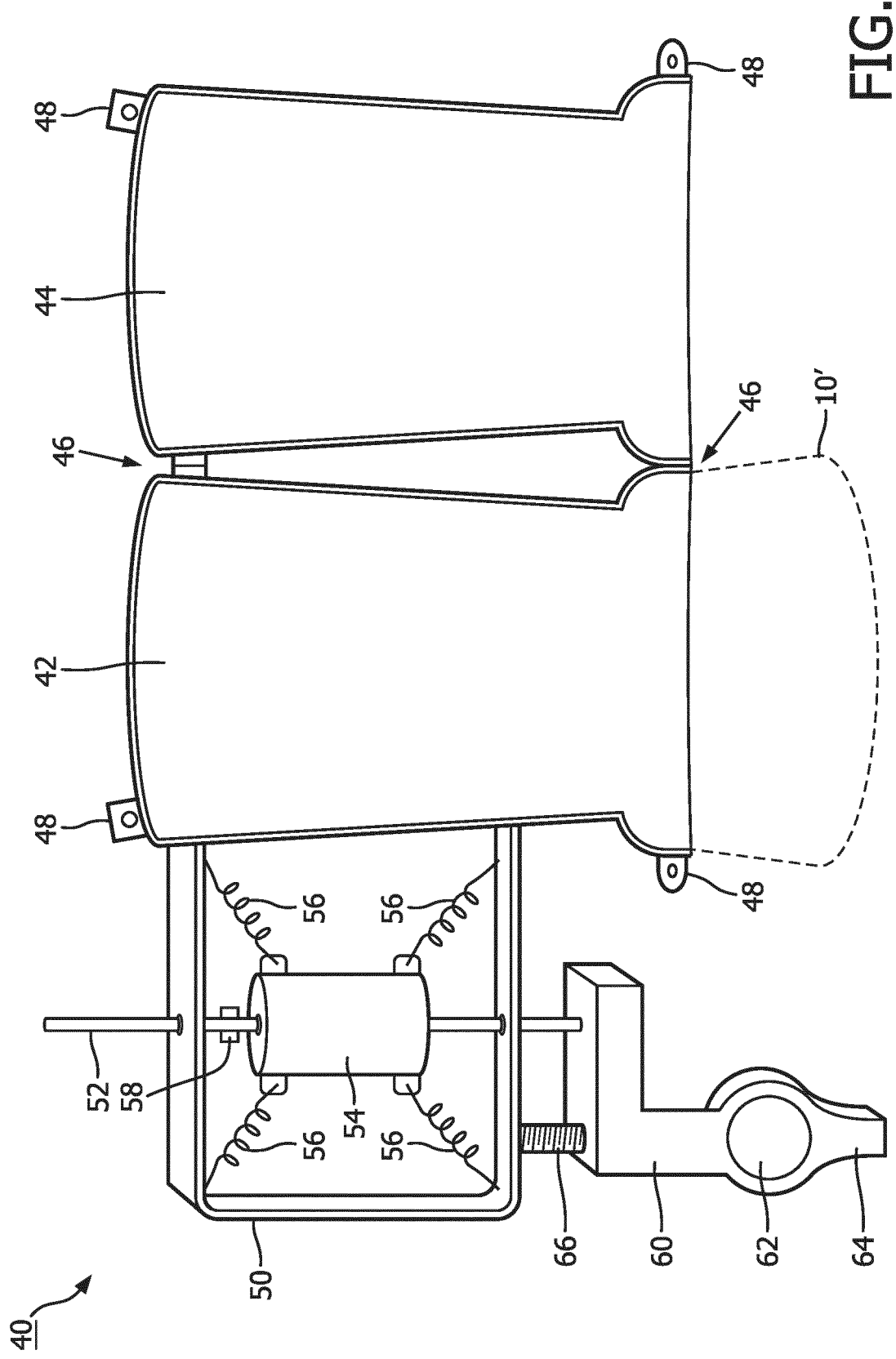
FIG. 2 illustrates a first implementation of a vibrator assembly constructed in accordance with the principles of the present invention.

FIG. 2 illustrates a first implementation of a vibrator assembly for an ultrasound probe constructed in accordance with the principles of the present invention. The vibrator assembly of FIG. 2 comprises an element for attaching the assembly to an ultrasound probe. The probe attachment element in the illustrated implementation comprise a clamshell-like arrangement of plastic shell halves 42 and 44 which are sized and shaped to fit securely to a conforming ultrasound probe when the two clamshell halves are closed around the probe. The clamshell halves are hinged to each other at 46 so that the right half 44 can be closed over the probe and secured to the left half 42 by tabs 48 which contain attracting magnets. Latching elements other than magnets can alternatively be employed to securely hold the clamshell halves in attachment to a probe. It will be appreciated that other mechanisms may alternatively be used to attach the vibrator assembly to a probe, such as straps, clips, or clamps that securely attach the assembly to the probe.

A vibration motor assembly 40 is attached to and extends from the left clamshell half 42. The vibration motor assembly comprises a frame 50. Mounted inside the frame 50 is a sleeve 54 with a slider 52 freely passing through a vertical aperture in the sleeve. The sleeve is suspended in the frame by four tension springs 56, which act as vibration isolation elements to reduce the coupling of vibratory energy from the sleeve to the frame. Other resilient or elastic elements can alternatively be used in place of the tension springs such as rubber bands or elastic strips. A retention element such as a clip, bracket, or nut 58 is attached to the slider above the sleeve to prevent the slider from falling out of the sleeve.

The slider 52 in this implementation extends through apertures in the frame 50 as shown in the drawing and a vibration motor mount 60 is attached to the lower end of the slider. A vibration motor 62 is located in the mount 62. The vibration motor mount 60 terminates in a narrowed lower end 64 which contacts a body for transmission of vibratory energy into the body during use of the assembly. A compression spring 66 located between the frame 50 and the vibration motor mount 60 urges the motor mount downward into contact with the body during use of the assembly. As can be seen by the relative positions of the lower end of the motor mount and the acoustic aperture of the ultrasound probe, indicated by the dashed outline 10' of the probe's acoustic aperture, the end of the motor mount extends beyond the face of the probe before the probe and assembly are brought into contact with a body, but is urged into continuous firm contact with the body by the compression spring 66 when the probe face is pressed against the body for scanning.

It is seen that the resilient tension springs that suspend the sleeve 54 in the frame 50 also provide vibration isolation of the sleeve, which guides the slider 52, from the frame. The vibration transmissibility of the assembly is the ratio between the transmitted amount of vibration ω (displacement and force) to the vibration ωn of the source, the vibration motor 62, its mount 60, and slider 52. The frequency ratio r of the vibration motor, its mount and the slider is calculated as $$= \frac{\omega}{\omega n}.$$

The natural frequency of the vibration motor, its mount, and the slider is given by $$= \sqrt{\frac{k}{m}},$$

where k represents the stiffness of the tension elements, in this case, springs 56, and m is the mass of the vibration motor assembly. The vibration energy transmitted to the frame 50 by springs 56 becomes lower than the vibration of the vibration motion at r>1.5. The greater the increase of r beyond the value of 1.5, the greater the isolation that is obtained. When r has been increased to a value of 3, significant transmission of vibration energy approaches zero. Thus, it is desirable to maximize r to a value of three or greater.

The r variable can be increased by decreasing the stiffness of the tension springs 56 and the compression spring 66 in the implementation of FIG. 2. The vibration frequency ω of the vibrator is essentially the rotational frequency of the vibration motor. By increasing the vibration frequency of the motor, vibration isolation will improve. But variation of this parameter is generally limited by the range of operation of the vibration motor, i.e., its maximum operational voltage and current. The natural frequency of the vibrator assembly depends on two main factors: the stiffness of springs 56 and the mass of the ultrasound probe. Increasing the mass of the probe will thus improve vibration isolation. However, the mass of the probe is generally a given, and increasing its mass is not practical. Thus, the practical approach to increasing r is to select spring elements with as low a stiffness value as possible, while still maintaining sufficient stiffness to support the weight of the sleeve 54.

Figure 3:
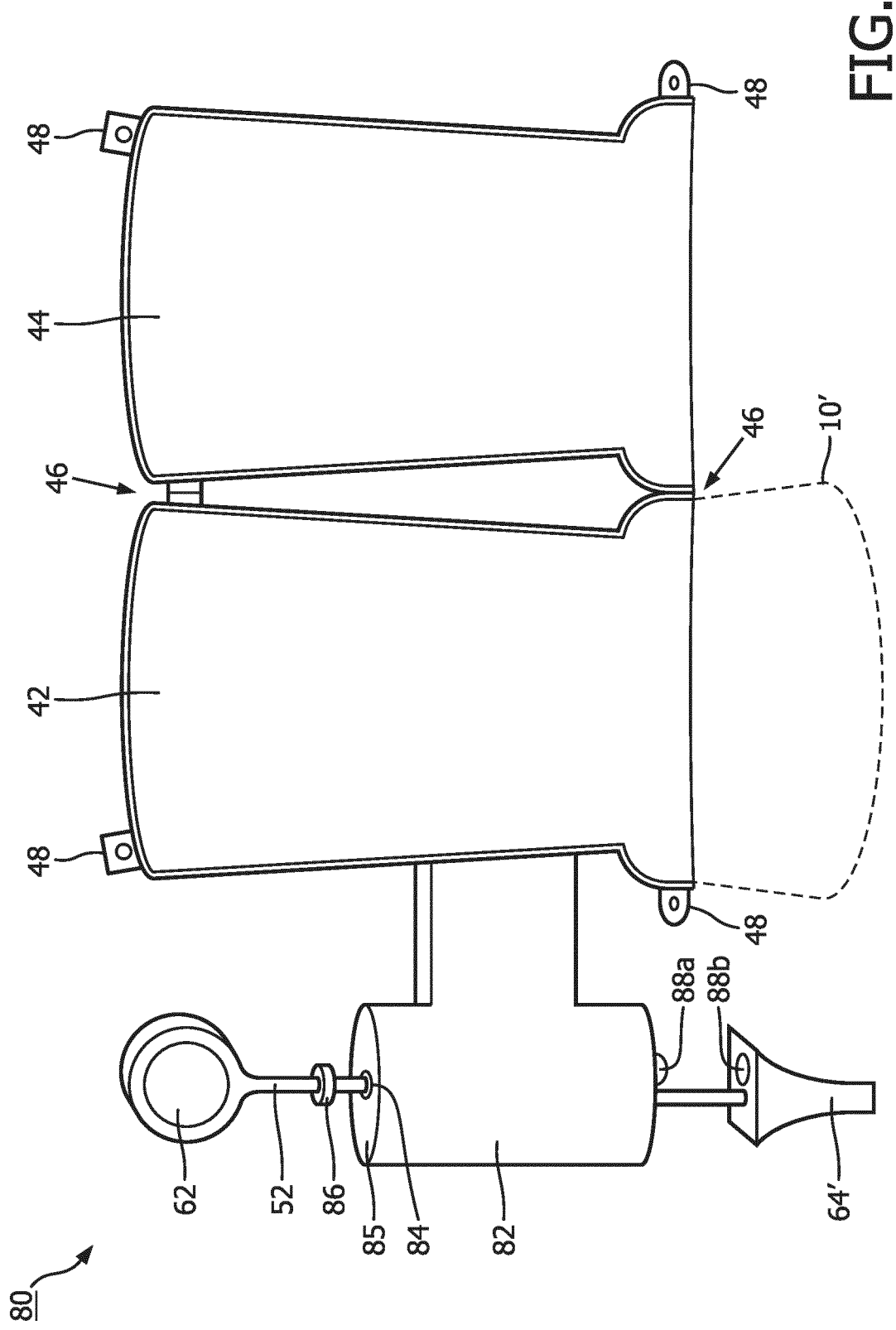
FIG. 3 illustrates a second implementation of a vibrator assembly constructed in accordance with the principles of the present invention.

FIG. 3 illustrates a second implementation of a vibrator assembly for an ultrasound probe constructed in accordance with the principles of the present invention. Elements common to both implementations bear the same reference numerals and will not be described again in the description of FIG. 3. As in the first implementation, a pair of hinged clamshell halves 42 and 44 are sized and shaped to fit snugly around an ultrasound probe, and fasten shut by magnets on opposing tabs 48 when the clamshell halves are closed around the probe. A vibration motor assembly 80 extends from the left clamshell half 42. This assembly 80 comprises a cylinder 82. The cylinder 82 contains a centrally located hollow sleeve 84 which is surrounded and retained in place by a filling 85 of soft silicone rubber or other elastic compound material. Located through the sleeve 84 and freely movable therethrough is a slider 52. Mounted at the top of the slider is a vibration motor 62. A rubber grommet or nut 86 is located on the slider above the cylinder and sleeve and limits a downward fall of the slider and motor when the apparatus is not in contact with a body.

A body engagement member 64' is mounted on the lower end of the slider and, like the lower end of the vibration motor mount 60 of FIG. 2, terminates in a blunt fin-like end which transmits vibrations into a contacted body. The body engagement member 64' is urged downward against the body by two opposing magnets 88a and 88b, which are mounted on the bottom of the cylinder 82 and the top of the member 64', and are poled to repel each other. Thus, the repulsive force of the opposing magnets will cause the member 64' to constantly be urged into firm contact with a body during use of the assembly. The magnets 88a and 88b serve the purpose of the compression spring 66 in FIG. 2.

It is seen that the soft silicone filling 85 which surrounds the sleeve 84, like the tension springs 56 in FIG. 2, serves to isolate vibration energy of the motor from the cylinder 82, the clamshell halves clamped around the ultrasound probe, and the probe itself. Thus, vibration energy which could corrupt the reception of ultrasound waves by the probe is isolated from the probe.

Figure 4:
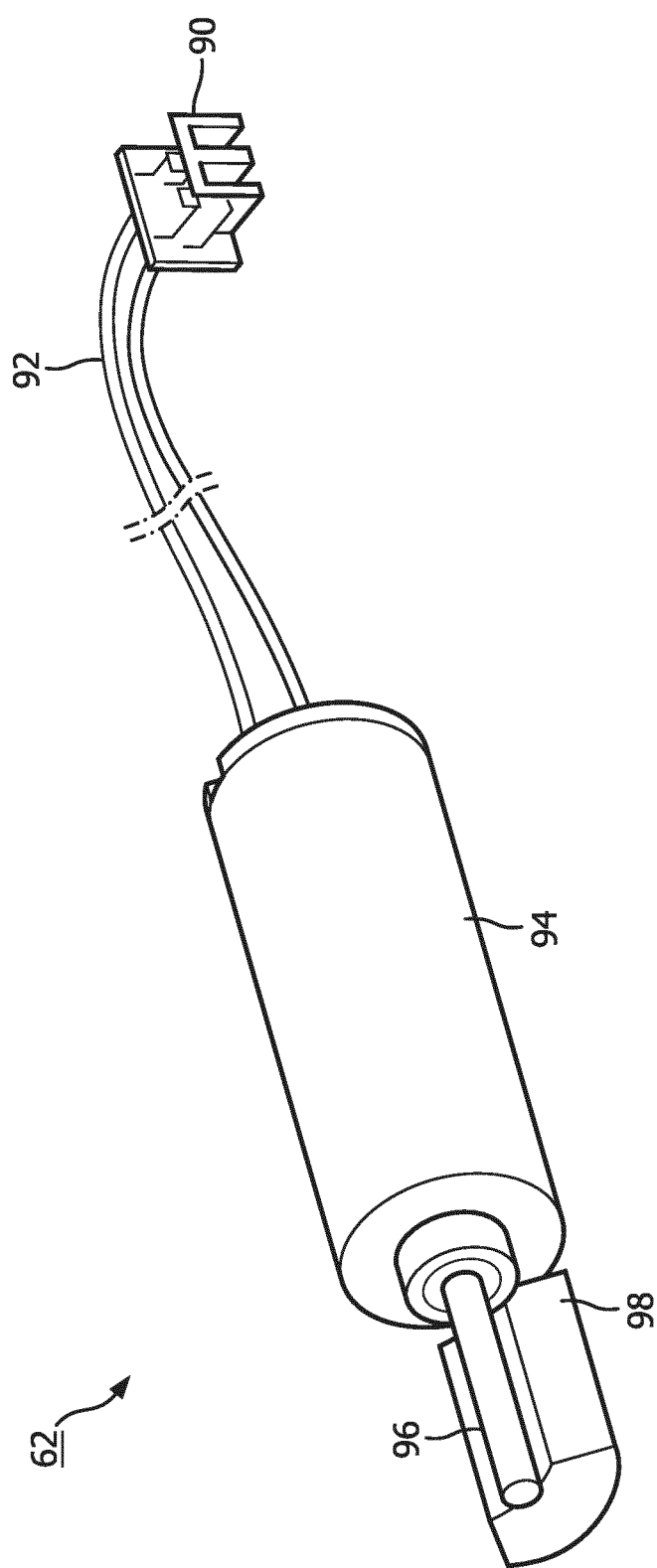
FIG. 4 illustrates a vibration motor suitable for use in a vibrator assembly of the present invention.

FIG. 4 illustrates a typical vibration motor 62 which can be used in either of the implementations of FIGS. 2 and 3. Located in a cylindrical body 94 is a DC motor which rotates a shaft 96. Mounted eccentrically on the shaft 96 is a weight 98. As the motor rotates the shaft, the eccentricity of the mounted weight causes the motor to vibrate. It is these vibrations which are conducted into a body to produce shear waves for ultrasonic measurement of tissue stiffness. A connector 90 is coupled to a DC voltage supply to provide the necessary drive voltage over wires 92 to power the vibration motor 62. Since the vibration is produced continuously while the vibration motor is powered, a continuous series of shear waves will be produced in the body for measurement, and there is therefore no need to synchronize operation of the ultrasound probe to shear wave generation.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system and its controller, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as a memory for the reference value map for the attenuation coefficient estimator 50 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine. The set of instructions of an ultrasound system including those controlling the acquisition, processing, and display of ultrasound images or shear wave measurements as described above may include various commands that instruct a computer or processor as a processing machine to perform specific operations such as the methods and processes of shear wave detection and measurement. The set of instructions may be in the form of a software program. The software may be in various forms such as system software or application software and which may be embodied as a tangible and non-transitory computer readable medium. The equations given above for the different methods for attenuation coefficient estimation and mapping, as well as the calculations used to produce the shear wave velocity display maps described above, are typically calculated by or under the direction of software routines. Further, the software may be in the form of a collection of separate programs or modules such as a velocity value mapping program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An apparatus for generating shear wave vibrations which are to be detected by an ultrasound probe comprising:
   a probe attachment element adapted to attach the apparatus to the ultrasound probe, wherein the probe attachment element comprises a pair of shells adapted to encompass at least a portion of the ultrasound probe when the pair of shells are attached to each other;

a vibration motor configured to generate vibration energy;

a vibration motor assembly, the vibration motor assembly comprising: (1) a sleeve; and (2) a slider adapted to move freely in the sleeve;

a vibration isolation element adapted to couple the vibration motor assembly to the probe attachment element; and a vibration motor mount comprising the vibration motor and coupled to one end of the slider, wherein the vibration motor mount couples the generated vibration energy to a body to generate the shear wave vibration, and wherein the vibration motor mount is moveable by the generated vibration energy.

2. The apparatus of claim 1, wherein the sleeve is coupled to the probe attachment element by the vibration isolation element.

3. The apparatus of claim 1, wherein the probe attachment element further comprises one or more straps.

4. The apparatus of claim 1, wherein the vibration isolation element further comprises a spring.

5. The apparatus of claim 4, wherein the vibration isolation element further comprises a plurality of springs.

6. The apparatus of claim 5, wherein the vibration isolation element further comprises a plurality of tension springs.

7. The apparatus of claim 1, wherein the vibration isolation element further comprises an elastic band.

8. The apparatus of claim 7, wherein the vibration isolation element further comprises a rubber band.

9. The apparatus of claim 1, wherein the vibration isolation element further comprises an elastic filling.

10. The apparatus of claim 9, wherein the vibration isolation element further comprises silicone rubber.

11. The apparatus of claim 1, wherein the vibration motor assembly further comprises:

an elastic compound retaining the sleeve in place; and a body engagement member mounted on the slider, wherein the elastic compound further comprises the vibration isolation element.

12. The apparatus of claim 11, further comprising a plurality of magnets adapted to urge the body engagement member into contact with a body by the force of repelling magnets, wherein the probe attachment element further comprises a container adapted to contain the elastic compound.

13. The apparatus of claim 12, wherein the container further comprises a cylinder; and wherein the elastic compound further comprises silicone rubber.

14. The apparatus of claim 1, wherein the vibration motor assembly comprises a frame encompassing the sleeve.

15. The apparatus of claim 14, wherein the vibration isolation element is configured to suspend the sleeve within the frame.

16. The apparatus of claim 14, wherein the slider is configured to move freely within the frame.

17. The apparatus of claim 14, wherein the vibration motor is positioned outside the frame.

18. The apparatus of claim 1, further comprising a resilient member configured to exert a resilient force biasing the vibration motor mount into contact with the body.

19. The apparatus of claim 18, wherein the resilient member is a compression spring or a magnet configuration.

* * * * *